United States Patent [19]

Takahashi et al.

[11] Patent Number: 5,012,004
[45] Date of Patent: Apr. 30, 1991

[54] ETHER COMPOUNDS AND THEIR PRODUCTION, AND INSECTICIDAL AND/OR ACARICIDAL COMPOSITIONS CONTAINING THEM

[75] Inventors: Junya Takahashi, Hyogo; Sumio Nishida, Takarazuka; Izumi Fujimoto, Minoo; Yoshinori Shono, Toyonaka; Hiroaki Fujimoto, Takarazuka, all of Japan

[73] Assignee: Sumitomo Chemical Company, Limited, Osaka, Japan

[21] Appl. No.: 265,892

[22] Filed: Nov. 2, 1988

[30] Foreign Application Priority Data

Nov. 4, 1987 [JP] Japan ............... 62-279585
Dec. 7, 1987 [JP] Japan ............... 62-310343
Jun. 1, 1988 [JP] Japan ............... 62-136021

[51] Int. Cl.$^5$ ............................................. C07C 319/00
[52] U.S. Cl. ............................ 568/53; 568/637; 568/640; 568/655
[58] Field of Search ............ 568/637, 655, 640, 53; 514/712, 721, 717

[56] References Cited

U.S. PATENT DOCUMENTS 3,963,786  6/1976  Karrer et al. ............... 568/637
4,057,587 11/1977  Karrer et al. ............... 568/637
4,552,894 11/1985  Inoue et al. ............... 514/464

OTHER PUBLICATIONS

Smirnova et al, *Chemical Abstracts*, vol. 53, No. 1243d (1959).

*Primary Examiner*—Bruce Gray
*Attorney, Agent, or Firm*—Birch, Stewart, Kolasch & Birch

[57] ABSTRACT

An insecticidal and/or acaricidal composition which comprises as an active ingredient an insecticidally and-/or acaricidally effective amount of at least one ether compound of the formula:

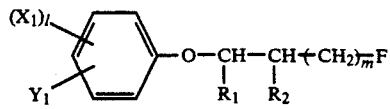

wherein $X_1$ is a hydrogen atom, a halogen atom, a lower alkyl group, a halo(lower)alkyl group, a phenoxyphenoxy(lower)alkyl group, a lower alkoxy group, a halo(lower)alkoxy group, a phenyl group, a halo(lower)alkoxyphenyl group, a methylenedioxy group or a group of the formula:

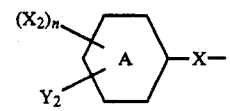

(in which

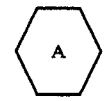

is a 6-membered unsaturated ring, $X_2$ is a hydrogen atom, a halogen atom or a halo(lower)alkoxy group, $Y_2$ is a hydrogen atom or combined with $Y_1$ to form a direct single bond, n is an integer of 1 or 2 and X is an oxygen atom, a sulfur atom, a carbonyl group or a group of the formula: —C($R_3$)($R_4$)— (in which $R_3$ and $R_4$ are each a hydrogen atom or a lower alkyl group));

$Y_1$ is a hydrogen atom or combined with $Y_2$ to form a direct single bond;

$R_1$ and $R_2$ are each a hydrogen atom or a lower alkyl group;

l is an integer of 1 or 2; and m is an integer of 0 to 2.

5 Claims, No Drawings

ETHER COMPOUNDS AND THEIR PRODUCTION, AND INSECTICIDAL AND/OR ACARICIDAL COMPOSITIONS CONTAINING THEM

The present invention relates to ether compounds and their production, and insecticidal and/or acaricidal compositions containing them.

Some ether compounds are known to exert an insecticidal or acaricidal activity (U.S. Pat. No. 4,552,894). However, thier insecticidal and/or acaricidal effect is not necessarily satisfactory.

As a result of extensive studies, it has now been found that an ether compound of the formula:

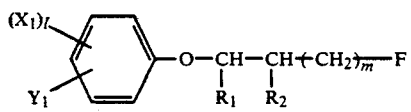

wherein $X_1$ is a hydrogen atom, group, a halo(lower)alkyl group, a phenoxyphenoxy(lower)-alkyl group, a lower alkoxy group, a halo(lower)alkoxy group, a phenyl group, a halo(lower)alkoxyphenyl group, a methylenedioxy group or a group of the formula:

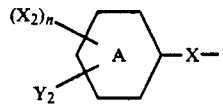

(in which

is a 6-membered unsaturated ring, $X_2$ is a hydrogen atom, a halogen atom or a halo-(lower)alkoxy group, $Y_2$ is a hydrogen atom or combined with $Y_1$ form a direct single bond, n is an integer of 1 or 2 and X is an oxygen atom, a sulfur atom, a carbonyl group or a group of the formula: $-C(R_3)(R_4)-O$ (in which $R_3$ and $R_4$ are each a hydrogen atom or a lower alkyl group));

$Y_1$ is a hydrogen atom or combined with $Y_2$ to form a direct single bond;

$R_1$ and $R_2$ are each a hydrogen atom or a lower alkyl group;

l is an integer of 1 or 2; and m is an integer of 0 to 2, exhibits a prominent insecticidal and/or acaricidal activity.

In the above significances, the term "halogen" or "halo" intends to mean fluorine, chlorine, bromine and iodine, inclusively. The term "lower" generally means a group having not more than 5 carbon atoms, particularly from 1 to 4 carbon atoms. The 6-membered unsaturated ring represented by

may be, for instance, cyclohexene, cyclohexadiene or benzene.

Accordingly, a main object of this invention is to provide an insecticidal and/or acaricidal composition comprising at least one of the ether compounds of the formula (I) as an active ingredient. Another object of the invention is to provide novel ether compounds of the formula (I). A further object of the invention is to provide a process for preparing novel ether compounds of the formula (I). These and other objects will be apparent from the foregoing and subsequent descriptions.

Specific examples of the harmful insects and acarids against which the ether compounds (I) of the invention exert their insecticidal or acaricidal activity are Hemiptera (e.g. delphacid planthoppers, leafhoppers, aphids, stink bugs, whiteflies), Lepidoptera (diamondback moth, rice stem borer, rice leafroller, cabbage armyworm, rice looper, common white, casemaking clothes moth, webbing clothes moth), Diptera (common gnat, Anopheles mosquito, house fly), Dictyoptera (German cockroach, smorkybrown cockroach, brown cockroach, American cockroach), Coleoptera, Hymenoptera, Diptera, Orthoptera, Tetranychidae (e.g. carmine spider mite, two-spotted spider mite, citrus red mite), etc.

The insecticidal and/or acaricidal activities of the ether compounds (I) are exerted on adults, larvae, nymphs, eggs, etc. of harmful insects and acarids as above exemplified. Also, their efficacy extends to harmful insects and/or acarids having developed resistance to conventional insecticides and/or acaricides.

Among the ether compounds (I), those of the following formula are novel:

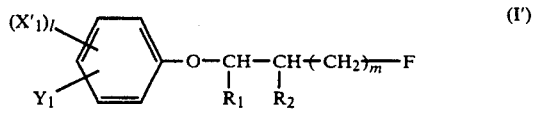

wherein $X_140$ is a fluoro(lower)alkyl group, a bromo(lower)alkyl group, an iodo(lower)alkyl group, a phenoxyphenoxy(lower)-alkyl group, a lower alkoxy group, a halo(lower)alkoxy group, a phenyl group, a halo(lower)alkoxyphenyl group, a methylenedioxy group or a group of the formula:

in which X' is an oxygen atom, a sulfur atom, a carbonyl group or a group of the formula: $-CH(R_3)-$, and

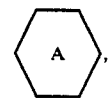

$X_2$, $Y_1$, $Y_2$, $R_1$, $R_2$, $R_3$, $l$, $m$ and $n$ are each as defined above.

From the viewpoint of high activity and broad spectrum, preferred are those of the formula:

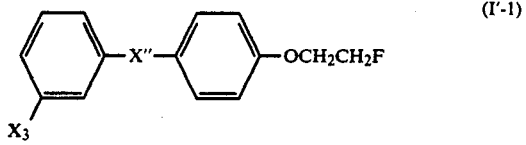
(I'-1)

wherein $X_3$ is a hydrogen atom or a fluorine atom and $X''$ is an oxygen atom, a sulfur atom or a methylene group, and of the formula:

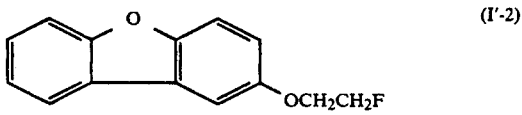
(I'-2)

Some of the ether compounds (I) are known, and their examples are shown in Table 1.

TABLE 1

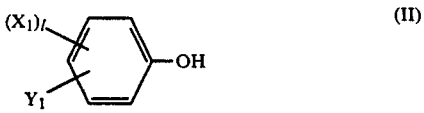

| W | Literature |
|---|---|
| 2-F; 3-F; 2-Cl; 3-Cl; 2-I; 3-I | Zh. Vses. Khim. Obshestva im. D. I. Mendeleeva 8, 115 (1963) |
| H; 4-F; 4-Cl; 4-Br | Izvest.Vysshikh Ucheb. Zavedenil. Khim. i Khim. Tekhnol., 1958, No. 2, 82 |
| 4-CH$_3$; 4-C$_2$H$_5$; 4-C$_3$H$_7$(i) | Zh. Vses. Khim. Obshestva im. D. I. Mendeleeva 7, 710 (1962) |
| 3-CH$_2$Cl; 4-CH$_2$Cl | German Offen. DE-3,402,483 |
| 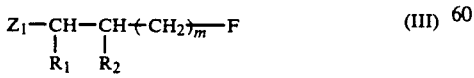 | USSR Patent 114,843 |

The ether compounds (I) of the invention can be prepared by various procedures, of which typical examples are shown below Procedure (a)

A phenol of the formula:

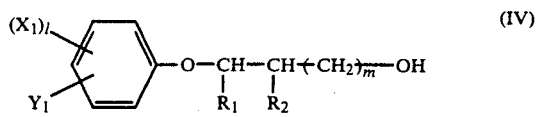
(II)

wherein $X_1$, $Y_1$, and $l$ are each as defined above is reacted with a compound of the formula:

$$Z_1-CH-CH+CH_2)_{\overline{m}}-F \quad \text{(III)}$$
$$\quad\quad | \quad\; |$$
$$\quad\quad R_1 \; R_2$$

wherein $R_1$, $R_2$ and $m$ are each as defined above and $Z_1$ is a halogen atom, a mesyloxy group or a tosyloxy group to give the ether compound (I).

The reaction is usually performed in an inert solvent in the presence of a base at a temperature of 0 to 120° C.,
preferably of room temperature to 90° C. For the reaction, the compound (III) is normally used in an amount of 0.7 to 1.4 moles to one mole of the phenol (II). As the inert solvent, there may be used dimethylformamide, tetrahydrofuran, acetonitrile, chloroform, toluene, water, etc., or their mixtures. Examples of the base are an organic base (e.g. triethylamine, pyridine), an inorganic base (e.g. sodium hydride, sodium hydroxide, potassium hydroxide, sodium carbonate, potassium carbonate), etc. The reaction is usually accomplished instantaneously or within 30 hours.

After completion of the reaction, the reaction mixture may be poured onto ice-water and subjected to post-treatment such as extraction with an organic solvent and concentration. If necessary, the reaction product may be further purified, for instance, by chromatography, recrystallization or distillation.

Procedure (b)

An alcohol of the formula:

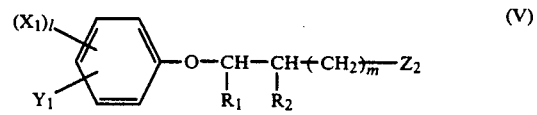
(IV)

wherein $X_1$, $Y_1$, $R_1$, $R_2$, $l$, and $m$ are each as defined above is fluorinated to give the ether compound (I).

The fluorination is usually achieved by treatment of the compound (IV) with a fluorinating agent in an inert solvent at a temperature of 0° C. to room temperature. The fluorinating agent is usually used in an amount of 0.25 to 10 moles to one mole of the compound (IV). As the fluorinating agent, there may be used sulfur tetrafluoride, dimethylaminosulfur trifluoride, diethylaminosulfur trifluoride or the like. Examples of the inert solvent are dichloromethane, chloroform, carbon tetrachloride, 1,2-dichloroethane, etc. The reaction is usually perfected instantaneously or within 30 hours.

After completion of the reaction, the reaction mixture is treated in the same manner as in Procedure (a).

In the above procedure, the group $X_1$ in the starting compound (IV) may represent any one convertible into a fluorine-containing group (e.g. difluoromethyl, fluoro(lower)alkoxy) on the fluorination. Examples of the group $X_1$ in such case are formyl and hydroxy(lower)alkoxy. During the fluorination, $X_1$ is simultaneously converted into the fluorine-containing group. For instance, formyl is converted into difluoromethyl. Further, for instance, 2-hydroxyethyloxy is converted into 2-fluoroethyloxy.

Procedure (c)

A compound of the formula:

$$\text{(X}_1\text{)}_l\text{-aryl-}O-CH-CH+CH_2)_{\overline{m}}-Z_2 \quad \text{(V)}$$
$$\quad\quad\quad\quad\quad\quad | \quad\; |$$
$$\quad\quad\quad\quad\quad\quad R_1 \; R_2$$

wherein $X_1$, $Y_1$, $R_1$, $R_2$, $l$, and $m$ are each as defined above and $Z_2$ is a halogen atom, a mesyloxy group or a tosyloxy group is reacted with a fluorinating agent to give the ether compound (I).

The reaction is ordinarily carried out by treatment of the compound (V) with a fluorinating agent in an inert solvent (e.g. ethylene glycol, N,N-dimethylformamide, dimethylsulfoxide, N-methyl-2-pyrrolidone, acetonitrile, sulphorane, tetrahydrofuran), preferably in the presence of a phase transfer catalyst at a temperature of 0° C to the refluxing point of the solvent. The fluorinating agent is usually employed in an amount of 0.8 to 10 moles to one mole of the compound (V). As the fluorinating agent, there may be used a metal fluoride (e.g. potassium fluoride, cesium fluoride, silver fluoride, cuprous fluoride), a fluorine-containing quarternary ammonium salt (e.g. tetrabutylammonium fluoride, tetraethylammonium fluoride), etc. Examples of the phase transfer catalyst are crown ethers (e.g. 18-crown-6), tetrabutylammonium bromide, etc. The reaction is normally accomplished instantaneously or within 30 hours.

After the reaction, the reaction mixture is treated in the same manner as in Procedure (a).

Practical and presently preferred embodiments for preparation of the ether compounds (I) are illustratively shown in the following Examples.

Example 1 (Procedure (a))

To a suspension of sodium hydride (60 % oil dispersion; 4.0 g) in N,N-dimethylformamide (100 ml), 2-phenylphenol (17.0 g) was added at a temperature of 0 to 5° C., and the resultant mixture was stirred at room temperature for 1 hour. 2-Fluoroethyl methanesulfonate (14.2 g) was added thereto. The resulting mixture was heated to 90° C., followed by stirring for 5 minutes. The reaction mixture was poured onto ice-water and extracted with ethyl acetate. The extract was washed with aqueous potassium carbonate solution, dried over anhydrous magnesium sulfate and concentrated under reduced pressure. The residue was purified by silica gel column chromatography (eluting solvent, toluene) to give 1-(2-fluoroethoxy)-2-phenylbenzene (Compound No. 20) (16.4 g). $n_D^{24.8}$ 1.5796.

Example 2 (Procedure (b))

To a solution of diethylaminosulfur trifluoride (5.0 g) in methylene chloride (50 ml), 2-(4-formylphenoxy)-ethanol (1.7 g) was added at 0° C, and the resultant mixture was stirred at room temperature for 12 hours. The reaction mixture was subjected to post-treatment as in Example 1 to give 1-difluoromethyl-4-(2-fluoroethoxy)benzene (Compound No. 10) (1.6 g).

NMR (TMS-CDCl$_3$)δ:7.40 (d, 2H), 6.90 (d, 2H), 6.55 (t, 1H), 5.00 –5.20 (m, 1H), 4.20 –4.45 (m, 2H), 3.85–4.00 (m, 1H).

Example 3 (Procedure (a))

To a suspension of sodium hydride (60% oil dispersion; 4.0 g) in N,N-dimethylformamide (100 ml), 4-phenoxyphenol (18.6 g) was added at a temperature of 0 to 5° C., and the resultant suspension was stirred at room temperature for 1 hour. 2-Fluoroethyl methanesulfonate (14.2 g) was added thereto. The resulting mixture was stirred at room temperature for 12 hours. The reaction mixture was subjected to post-treatment as in Example 1 to give 1-(2-fluoroethoxy)-4-phenoxybenzene (Compound No. 22) (20.0 g). $n_D^{25.0}$ 1.5622.

Example 4 (Procedure (b))

Diethylaminosulfur trifluoride (16.2 g) was dissolved in dry dichloromethane (200 ml) under nitrogen stream, and the resultant solution was cooled to 0° C. 2-[4-(3-Fluorophenoxy)phenyl]ethanol (24.8 g) was dropwise added thereto. The resulting mixture was stirred at room temperature for 12 hours. The reaction mixture was subjected to post-treatment as in Example 1 to give 1-(2-fluoroethoxy)-4-(3-fluorophenoxy)benzene (Compound No. 23) (19.5 g). $n_D^{26.7}$ 1.5452.

Example 5 (Procedure (a))

To a suspension of sodium hydride (60% oil dispersion; 4.0 g) in N,N-dimethylformamide (100 ml), 2-hydroxydibenzofuran (18.4 g) was added at a temperature of 0 to 5° C., and the resultant suspension was stirred at room temperature for 1 hour. 2-Fluoroethyl methanesulfonate (14.2 g) was added thereto. The resulting mixture was stirred at room temperature for 12 hours. The reaction mixture was poured into ice-water and extracted with ethyl acetate. The extract was washed with aqueous potassium carbonate solution, dried over anhydrous magnesium sulfate and concentrated under reduced pressure. The residue was distilled under reduced pressure to give 2-(2-fluoroethoxy)-dibenzofuran (Compound No. 35) (19.6 g). b.p., 180°–185° C./5 mmHg.

Example 6 (Procedure (b))

Diethylaminosulfur trifluoride (16.2 g) was dissolved in dry dichloromethane (200 ml) under nitrogen stream, and the resultant solution was cooled to 0° C. 2-(2-Dibenzofuryl)ethanol (22.8 g) was dropwise added thereto. The resulting mixture was stirred at room temperature for 12 hours. The reaction mixture was subjected to post-treatment as in Example 1 to give 2-(2-fluoroethoxy)dibenzofuran (Compound No. 35) (19.5 g). The boiling point of this product was almost identical to that of the compound obtained in Example 5.

In the same manner as above, the ether compounds (I) as shown in Table 2 were obtained.

TABLE 2

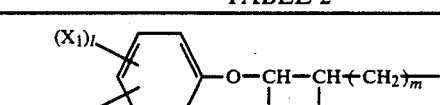

| Compound No. | (X$_1$)$_l$, Y$_1$ structure | R$_1$ | R$_2$ | m | Physical property |
|---|---|---|---|---|---|
| 1 | (phenyl) | H | H | 0 | b.p. 80–85° C./20 mmHg |

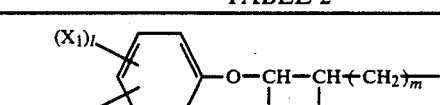

TABLE 2-continued $$\underset{Y_1}{\overset{(X_1)_l}{\bigcirc}}-O-\underset{R_1}{\overset{|}{C}H}-\underset{R_2}{\overset{|}{C}H}+CH_2\!\!\!\!\!-_m\!F \qquad (I)$$

| Compound No. | (X₁)ₗ / Y₁ aryl | R₁ | R₂ | m | Physical property |
|---|---|---|---|---|---|
| 2 | 4-F-C₆H₄- | H | H | 0 | b.p. 90–95° C./20 mmHg |
| 3 | 2-Cl-C₆H₄- | H | H | 0 | b.p. 116–120° C./20 mmHg |
| 4 | 3-Cl-C₆H₄- | H | H | 0 | b.p. 110–115° C./20 mmHg |
| 5 | 3-CH₃O-C₆H₄- | H | H | 0 | b.p. 126–130° C./20 mmHg |
| 6 | 2-CH₃-C₆H₄- | H | H | 0 | $n_D^{27.3}$ 1.4951 |
| 7 | 3-CH₃-C₆H₄- | H | H | 0 | $n_D^{27.5}$ 1.4979 |
| 8 | 4-CH₃-C₆H₄- | H | H | 0 | $n_D^{27.5}$ 1.4981 |
| 9 | 4-Cl-2-CH₃-C₆H₃- | H | H | 0 | NMR (TMS-CDCl₃) δ: 6.80–7.20 m, 3H), 5.00–5.20 (m, 1H), 4.20–4.40 (m, 2H), 3.80–4.00 (m, 1H), 2.20 (s, 3H) |
| 10 | 4-CHF₂-C₆H₄- | H | H | 0 | NMR (TMS-CDCl₃) δ: 7.40 (d, 2H), 6.90 (d, 2H), 6.55 (t, 1H), 5.00–5.20 (m, 1H), 4.20–4.45 (m, 2H), 3.85–4.00 (m, 1H) |
| 11 | 4-FCH₂CH₂O-C₆H₄- | H | H | 0 | $n_D^{25.0}$ 1.4766 |

TABLE 2-continued
$$\begin{array}{c}(X_1)_l\\ \diagdown\\ \diagup\\ Y_1\end{array}\!\!-\!\!O\!-\!\!\underset{R_1}{CH}\!-\!\underset{R_2}{CH}\!\!\!-\!\!(CH_2)_m\!-\!F \quad (I)$$
| Compound No. | (X₁)ₗ—⟨⟩—Y₁ | R₁ | R₂ | m | Physical property |
|---|---|---|---|---|---|
| 12 | 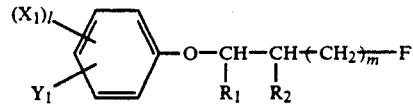 FCH₂CH₂O—⟨⟩—⟨⟩— | H | H | 0 | NMR (TMS-CDCl₃ + DMSO-d₆) δ: 7.60 (d, 4H), 7.10 (d, 4H), 5.10–5.30 (m, 2H), 4.30–4.60 (m, 4H), 4.00–4.30 (m, 2H) |
| 13 | 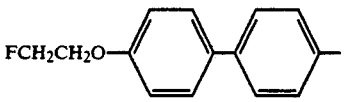 | H | H | 0 | $n_D^{29.2}$ 1.5176 |
| 14 | 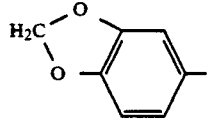 | H | H | 0 | $n_D^{26.0}$ 1.5588 |
| 15 | 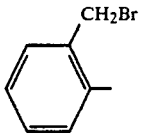 | H | H | 0 | $n_D^{26.8}$ 1.5574 |
| 16 | 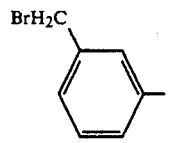 | H | H | 0 | $n_D^{27.1}$ 1.5642 |
| 17 | 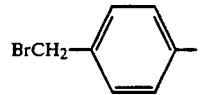 | H | H | 0 | $n_D^{26.5}$ 1.5871 |
| 18 | 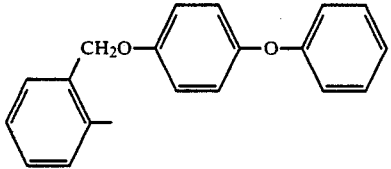 | H | H | 0 | $n_D^{26.5}$ 1.5889 |
| 19 | 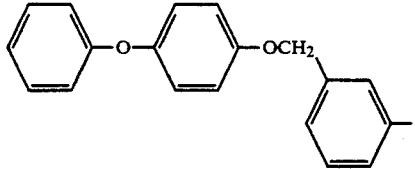 | H | H | 0 | NMR (TMS-CDCl₃) δ: 6.80–7.50 (m, 13H), 4.95 (s, 2H), 5.00–5.30 (m, 1H), 4.20–4.50 (m, 2H), 3.80–4.10 (m, 1H) |
| 20 | 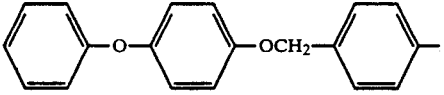 | H | H | 0 | $n_D^{24.8}$ 1.5796 |

TABLE 2-continued
$$\text{(X}_1\text{)}_l\text{—} \underset{Y_1}{\bigcirc}\text{—O—CH—CH}\underset{R_1\ R_2}{\text{—}}(\text{CH}_2)_m\text{—F} \quad (I)$$
| Compound No. | (X₁)ₗ—⟨⟩—<br>Y₁ | R₁ | R₂ | m | Physical property |
|---|---|---|---|---|---|
| 21 | 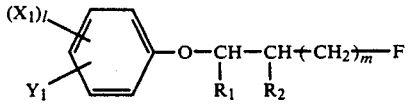 | H | H | 0 | $n_D^{24.9}$ 1.5908 |
| 22 | 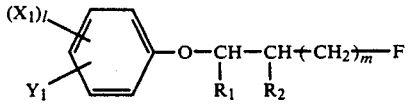 | H | H | 0 | $n_D^{25.0}$ 1.5622 |
| 23 | 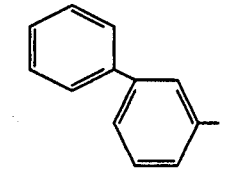 | H | H | 0 | $n_D^{26.7}$ 1.5452 |
| 24 | 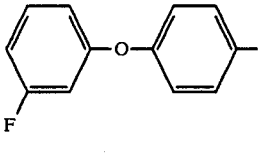 | H | H | 0 | $n_D^{26.8}$ 1.5309 |
| 25 | 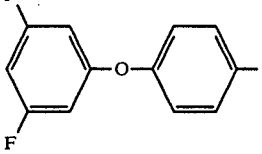 | H | H | 2 | $n_D^{27.0}$ 1.5471 |
| 26 | 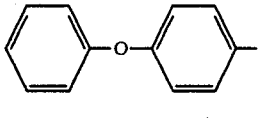 | CH₃ | H | 0 | $n_D^{27.0}$ 1.5508 |
| 27 | 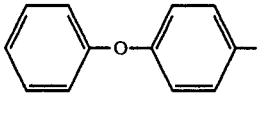 | H | CH₃ | 0 | $n_D^{27.0}$ 1.5505 |
| 28 | 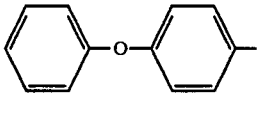 | H | C₂H₅ | 0 | $n_D^{27.0}$ 1.5489 |
| 29 | 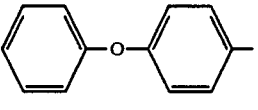 | H | H | 0 | $n_D^{28.5}$ 1.5618 |
| 30 | 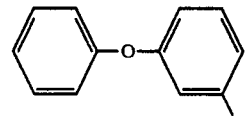 | H | H | 0 | $n_D^{28.5}$ 1.5598 |

TABLE 2-continued $$\underset{Y_1}{\overset{(X_1)_l}{\bigcirc}}-O-\underset{R_1}{CH}-\underset{R_2}{CH}+CH_2)_m-F \quad (I)$$

| Compound No. | $\underset{Y_1}{\overset{(X_1)_l}{\bigcirc}}-$ | $R_1$ | $R_2$ | m | Physical property |
|---|---|---|---|---|---|
| 31 | Ph-C(CH$_3$)$_2$-Ph- | H | H | 0 | $n_D^{27.0}$ 1.5558 |
| 32 | FCH$_2$CH$_2$O-Ph-C(CH$_3$)$_2$-Ph- | H | H | 0 | NMR (TMS-CDCl$_3$) δ: 7.20 (d, 4H), 6.83 (d, 4H), 5.10 (m, 2H), 4.35 (m, 4H), 3.95 (m, 2H), 1.65 (s, 6H) |
| 33 | Ph-S-Ph- | H | H | 0 | $n_D^{26.2}$ 1.5981 |
| 34 | FCH$_2$CH$_2$O-Ph-S-Ph- | H | H | 0 | NMR (TMS-CDCl$_3$) δ: 7.28 (d, 4H), 6.82 (d, 4H), 5.05 (m, 2H), 4.35 (m, 4H), 3.88 (m, 2H) |
| 35 | dibenzofuran- | H | H | 0 | b.p. 180–185° C./5 mmHg |
| 36 | Ph-C(=O)-Ph- | H | H | 0 | m.p. 59.5–60.5° C. |
| 37 | fluorenone- | H | H | 0 | NMR (TMS-CDCl$_3$) δ: 6.8–7.8 (m, 7H), 3.9–5.2 (m, 4H) |
| 38 | cyclohexyl-O-Ph- | H | H | 0 | $n_D^{24.0}$ 1.5265 |

On the application of the ether compound (I) as an insecticidal and/or acaricidal composition, it may be used as such or in an appropriate preparation form such as an oil spray, an emulsifiable concentrate, a wettable powder, a flowable, granules, a dust, an aerosol, a fumigant (e.g. mosquito coil, electric mosquito mat, low temparature fumigant), a smoking agent (e.g. self-combustible smoking agent, chemically reactive smoking agent, smoking agent for microporous ceramic plate), a non-heating vaporizing agent (e.g. resinous vaporizing agent, paper-impregnated vaporizing agent), an aerosol, a thermal fogging, an ultra low volume (ULV) spray, a toxic bait, etc. In those preparations, the ether compound (I) is usually contained in 0.01 to 95% by weight.

Said preparation can be formulated in a per se conventional manner by mixing at least one of the ether compounds (I) with an appropriate solid, liquid or gaseous carrier(s) or diluent(s). An appropriate adjuvant(s) such as a surfactant, an adherent, a dispersant or a stabilizer may be also mixed therein for improving the dispersibility and other properties of the preparation.

Examples of the solid carriers or diluents are clays (e.g. kaolin clay, diatomaceous earth, synthetic hydrated silica, attapulgite clay, bentonite, fubasami clay, terra alba), talcs, ceramics, other inorganic minerals (e.g. sericite, quartz, sulfur, active carbon, calcium carbonate, hydrated silica), chemical fertilizers (e.g. ammonium sulfate, ammonium phosphate, ammonium nitrate, urea, ammonium chloride), etc. Examples of the liquid carriers or diluents are alcohols (e.g. methanol, ethanol), ketones (e.g. acetone, methylethylketone), aromatic hydrocarbons (e.g. benzene, toluene, xylene, ethylbenzene, methylnaphthalene), aliphatic hydrocarbons (e.g. hexane, cyclohexane, kerosene, lamp oil), esters (e.g. ethyl acetate, butyl acetate), nitriles (e.g. acetonitrile, isobutyronitrile), ethers (e.g. diisopropyl ether, dioxane), acid amides (e.g. N,N-dimethylformamide, N,N-dimethylacetamide), halogenated hydrocarbons (e.g. dichloromethane, trichloroethane, carbon tetrachloride), dimethylsulfoxide, botanical oils (e.g. soybean oil, cotton-seed oil), etc. Examples of the gaseous carriers or diluents are Freon gas, butane gas, LPG (liquefied petroleum gas), dimethyl ether, carbon dioxide, etc.

The surfactants usable for emulsification, dispersion or spreading may be any of ionic and non-ionic types. Their examples are alkylsulfates, alkylsulfonates, alkylarylsulfonates, alkylaryl ethers, polyoxyethylene alkylaryl ether, polyethylene glycol ethers, polyvalent alcoholates and glycitols, etc. Examples of the adherents or dispersants may include casein, gelatin, polyvalent alcohols (e.g. starch powder, gum arabic, cellulose derivatives, alginic acid), lignin derivatives, bentonite, saccharides, synthetic aqueous high molecular compounds (e.g. polyvinyl alcohol, polyvinylpyrrolidone, polyacrylic acid), etc. As the stabilizers, there may be used alkyl phosphates (e.g. PAP (isopropyl acid phosphate), BHT (2,6-di-t-butyl-4-methyl-phenol), BHA (mixture of 2-t-butyl-4-methoxyphenol and 3-t-butyl-4-methoxyphenol), botanical oils, mineral oils, surfactans, aliphatic acids or esters, etc.

As the base or carrier for mosquito coil, there are used vegetable powders (e.g. wooden powders, lees) in combination with a binding agent (e.g. powders of *Machilus thunbergii*, starch, gluten). The base for electric mosquito mat is a hardened plate of fibrils comprising cotton linter, optionally admixed with pulp. The base for self-combustible smoking agent comprises an exothermic burning agent (e.g. nitrate, nitrite, guanidine salt, potassium chlorate, nitrocellulose, ethyl cellulose, wooden powders), a thermal decomposition initiator (e.g. alkaline earth metal salts, alkali metal salts, bichromates, chromates), an oxygen supplier (e.g. potassium nitrate), a burning support (e.g. melamine, wheat starch), an additive (e.g. diatomaceous earth), a binding agent (e.g. synthetic starch), etc. The base for chemically reactive smoking agent comprises an exothermic agent (e.g. alkali metal sulfides, alkali metal polysulfides, alkali metal hydrosulfides, calcium oxide), a catalytic agent (e.g. carbonaceous material, iron carbide, activated clay), a organic foaming agent (e.g. azodicarbonamide, benzenesulfonylhydrazide, dinitrosopentamethylenetetramine, polystyrene, polyurethane), a filler (e.g. natural fibers, synthetic fibers), etc. As the base for nonheating vaporizing agent, there may be used thermoplastic resins, filter papers, Japanese papers, etc. The base for toxic baits may comprise food (e.g. grain powders, essential oils, sugar, crystalline cellulose), an antioxidant (e.g. dibutylhydroxytoluene, nordihydroguaiaretic acid), a preservative (e.g. dehydroacetic acid), a mis-feed inhibitor (e.g. red pepper powders), a flavoring agent (e.g. cheese flavor, onion flavor), etc.

The ether compound (I) of the invention formulated into an appropriate preparation may be applied as such or in a form of dilution with water. In addition, said composition may contain other insecticides, nematocides, acaricides, soil vermin controlling agents, vermin controlling agents, fungicides, herbicides, plant growth regulators, synergistic agents, fertilizers, soil improvers, etc.

The dosage of the ether compound (I) as the active ingredient in an agricultural insecticidal and/or acaricidal composition is generally from 0.5 to 1000 grams, preferably from 5 to 500 grams, per 10 ares. When the composition is applied as an emulsifiable concentrate, a wettable powder or a flowable, the concentration of the active ingredient may be normally from 10 to 1000 ppm. In case of such formulation as dusts, granules, etc., the composition may be applied as such without diluting with water. As household insecticidal and/or acaricidal composition, the composition in the form of an emulsifiable concentrate, a wettable powder or a flowable is diluted with water in a concentration of the active ingredient being generally from 10 to 1000 ppm and applied. In case of the formulation such as an oil spray, an aerosol, a fumigant, a smoking agent, a vaporizing agent, a fogging agent, a ULV spray or a toxic bait, it may be applied as such.

Some practical embodiments of the composition for the control of insects and/or acarids according to the invention are illustratively shown in the following Formulation Examples wherein % and part(s) are by weight and the compound numbers correspond to those in Table 2.

Formulation Example 1

One of Compound Nos. 1 to 38 (0.2 part), xylene (2 parts), dimethylformamide (2 parts) and lamp oil (95.8 parts) are well mixed to make an oil spray.

Formulation Example 2

One of Compound Nos. 1 to 38 (10 parts), polyoxyethylene styrylphenyl ether (14 parts), calcium dodecylbenzenesulfonate (6 parts), xylene (35 parts) and dimethylformamide (35 parts) are well mixed to make an emulsifiable concentrate.

Formulation Example 3

One of Compound Nos. 1 to 38 (20 parts), fenitrothion (0,0-dimethyl-O-(3-methyl-4-nitrophenyl)phosphorothioate) (10 parts), calcium ligninsulfonate (3 parts), sodium laurylsulfate (2 parts) and synthetic hydrated silica (65 parts) are well mixed in a pulverizer to make a wettable powder.

Formulation Example 4

One of Compound Nos. 1 to 38 (1 part), carbaryl (1-naphthyl N-methylcarbamate) (2 parts), kaolin clay (87 parts) and talc (10 parts) are well mixed in a pulverizer to make a dust.

Formulation Example 5

One of Compound Nos. 1 to 38 (5 parts), synthetic hydrated silica (1 part), calcium ligninsulfonate (2 parts), bentonite (30 parts) and kaolin clay (62 parts) are well mixed in a pulverizer. To the resultant mixture, water is added, and the resulting mixture is kneaded well and granulated by the aid of a granulator, followed by dryig to give granules.

Formulation Example 6

One of Compound Nos. 1 to 38 (0.05 part), tetramethrin (N-(3,4,5,6-tetrahydrophthalimido)methyl chrysanthemate) (0.2 part), resmethrin (5-benzyl-3-furylmethyl (±)-cis,trans-chrysanthemate) (0.05 part), xylene (7 parts) and deodorized lamp oil (42.7 parts) are well mixed and charged into an aerosol container. Upon attachment of a valve portion, a pressurizing agent (LPG) (50 parts) is charged through the valve to make an aerosol.

Formulation Example 7

One of Compound Nos. 1 to 38 (0.3 g) is added to d-trans-allethrin (($\pm$)-3-allyl-2-methyl-4-oxo-2-cyclopentenyl d-trans-chrysanthemate) (0.3 g) in methanol (20 ml). The resultant mixture is combined with a base material for mosquito coil (powders of *Machilus thunbergii*:lees:wooden powders=3:5:1) (99.4 g) and uniformly mixed. After evaporation of methanol, water (150 ml) is added thereto and thoroughly mixed, molded and dried to make a mosquito coil.

The following Test Examples present some typical test data indicating the excellent insecticidal and/or acaricidal activities of the ether compounds (I). The compounds used for comparison are shown in Table 3 below:

TABLE 3

| Compound No. | Structure | Remarks |
|---|---|---|
| A | ⟨phenyl⟩—CH$_2$O—⟨phenyl⟩—OCH$_2$CH$_2$F | U.S. Pat. No. 4,552,894 |
| B | Cl—⟨phenyl with CH$_3$⟩—N=CH—N(CH$_3$)(CH$_3$) | Chlordimeform (N'-(4-chloro-2-methylphenyl)-N,N-dimethylformamidine) |

Test Example 1

Seven days after sowing, adults of diamondback moth (*Plutella xylostella*) were released to cotyledons of three radishes for oviposition (about 15 eggs per 1 cotyledon). The cotyledons were dipped in a 200 fold dilution (ca. 500 ppm) of an emulsifiable concentrate prepared according to Formulation Example 2 for 30 seconds. After air-drying, the seedlings were taken into a cup made of polyethylene at the bottom of which were placed a filter paper. Three days thereafter, mortality (%) of the eggs was observed with two replications. The results are shown in Table 4.

TABLE 4

| Compound No. | Mortality (%) |
|---|---|
| 1 | 100 |
| 2 | 100 |
| 3 | 100 |
| 4 | 100 |
| 5 | 100 |
| 6 | 100 |
| 7 | 100 |
| 8 | 100 |
| 9 | 100 |
| 10 | 100 |
| 11 | 100 |
| 12 | 100 |
| 13 | 100 |
| 14 | 100 |
| 15 | 100 |
| 16 | 100 |
| 17 | 100 |
| 18 | 100 |
| 19 | 100 |
| 20 | 100 |
| 21 | 100 |
| 22 | 100 |
| 23 | 100 |

TABLE 4-continued

| Compound No. | Mortality (%) |
|---|---|
| 24 | 100 |
| 25 | 100 |
| 26 | 100 |
| 27 | 100 |
| 28 | 100 |
| 29 | 100 |
| 30 | 100 |
| 31 | 100 |
| 32 | 100 |
| 33 | 100 |
| 34 | 100 |
| 35 | 100 |
| 36 | 100 |
| 37 | 100 |
| 38 | 100 |

Test Example 2

Stems of rice plants (about 12 cm in length) were dipped in a 200 fold dilution (ca. 500 ppm) of the emulsifiable concentrate prepared according to Formulation Example 2. After air-drying, the stems were taken into a test tube and 10 adults of brown rice planthopper (*Nilaparvata lugens*) were released therein. One day thereafter, mortality (%) was observed with two replications. The results are shown in Table 5.

TABLE 5

| Compound No. | Mortality (%) |
|---|---|
| 3 | 100 |
| 11 | 100 |
| 20 | 100 |
| 22 | 100 |
| 23 | 100 |
| 29 | 90 |
| 30 | 100 |
| 33 | 100 |
| A | 0 |
| Untreated | 5 |

Test Example 3

An emulsifiable concentrate prepared according to Formulation Example 2 was diluted with water to make a concentration of 3.5 ppm. The dilution (100 ml) was charged in a plastic cup (each 180 ml volume), and twenty last instar larvae of common mosquito (*Culex pipiens pallens*) were released therein. Feeding was continued until emergence of all larvae, and the rate of emergence inhibition was observed.

The rate of emergence inhibition was determined according to the following criteria:

Rate of emergence inhibition
a above 90% inhibition
b: less than 90% to not less than 80% inhibition
c: less than 80% inhibition The results are shown in Table 6.

TABLE 6

| Compound No. | Rate of emergence inhibition (%) |
|---|---|
| 9 | a |
| 11 | a |
| 18 | a |
| 19 | a |
| 21 | a |
| 22 | a |
| 23 | a |
| 24 | a |
| 25 | a |

TABLE 6-continued

| Compound No. | Rate of emergence inhibition (%) |
| --- | --- |
| 26 | a |
| 27 | a |
| 28 | a |
| 32 | a |
| 33 | a |
| 34 | a |
| 35 | a |
| A | b |
| Untreated | c |

Example 4

Adults of female carmine spider mites (*Tetranychus cinnabarinus*) were permitted to live on leaves (10 mites per leaf) of kidney bean seven days after sowing in the pots, and the mites were kept at 25° C. in a greenhouse. After 6 days, a 200 fold dilution (ca. 500 ppm) of the emulsifiable concentrate prepared according to Formulation Example 2 was sprayed over the pots placed on a turn table at a spray volume of 15 ml per pot, and also 2 ml of the dilution were applied to the soil in each pot. Eight days thereafter, the plant damage by the mites was observed and evaluated according to the following criteria:

—: no material damage to leaves
+: slight damage to leaves
++: same damage as seen in untreated plot The results are shown in Table 7.

TABLE 7

| Compound No. | Plant damage |
| --- | --- |
| 11 | − ~ + |
| 17 | − |
| 18 | − ~ + |
| 21 | − ~ + |
| 22 | − ~ + |
| 30 | − ~ + |
| 33 | − |
| 35 | − |
| 36 | − |
| 37 | − ~ + |
| 38 | − |
| B | + |

TABLE 7-continued

| Compound No. | Plant damage |
| --- | --- |
| Untreated | + |

What is claimed is:

1. An ether compound of the formula:

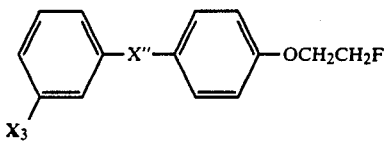

wherein $X_3$ is a hydrogen atom or a fluorine atom and $X''$ is an oxygen atom, a sulfur atom or a methylene group.

2. An ether compound of the formula:

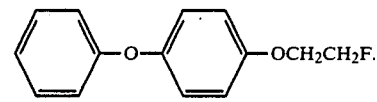

3. An ether compound of the formula:

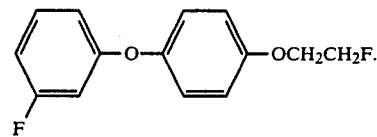

4. An ether compound of the formula:

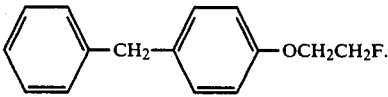

5. An ether compound of the formula:

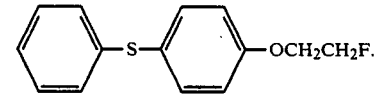

* * * * *